US006906185B1

(12) United States Patent
Fuller et al.

(10) Patent No.: US 6,906,185 B1
(45) Date of Patent: Jun. 14, 2005

(54) DERIVATIVES OF 7-DEAZA -2'-DEOXYGUANOSINE-5'-TRIPHOSPHATE, PREPARATION AND USE THEREOF

(75) Inventors: Carl W. Fuller, Cleveland Heights, OH (US); Mark McDougall, Columbus, OH (US); Shiv Kumar, Solon, OH (US)

(73) Assignee: Amersham Biosciences Corp., Piscataway, NJ (US)

(*) Notice: Subject to any disclaimer, the term of this patent is extended or adjusted under 35 U.S.C. 154(b) by 317 days.

(21) Appl. No.: 09/045,732

(22) Filed: Mar. 20, 1998

Related U.S. Application Data

(60) Provisional application No. 60/041,320, filed on Mar. 20, 1997.

(51) Int. Cl.[7] ...................... C07H 21/04; C07H 19/173; C12P 19/32
(52) U.S. Cl. .................... 536/23.1; 536/27.1; 536/25.3; 435/89
(58) Field of Search .............................. 536/23.1, 27.1, 536/25.3, 22.1, 27.12, 26.12, 26.1; 435/89

(56) References Cited

U.S. PATENT DOCUMENTS

| | | | |
|---|---|---|---|
| 4,435,569 A | * 3/1984 | Nishimura et al. | ......... 544/280 |
| 4,804,748 A | 2/1989 | Seela | ........................... 536/28 |
| 5,480,980 A | 1/1996 | Seela | ........................ 536/23.1 |
| 5,844,106 A | * 12/1998 | Seela et al. | ................. 536/22.1 |

FOREIGN PATENT DOCUMENTS

| WO | 93/09127 | 5/1993 |
| WO | WO 93/09127 | * 5/1993 |
| WO | 94/22892 | 10/1994 |

OTHER PUBLICATIONS

Seela FT et al, "Duplex Stabilization of DNA: Oligonucleotides Containing 7–Substituted 7–Deazaadenines", Helvetica Chimica Acta, vol. 78, Feb. 22, 1995, pp. 94–108.*
Mathews CK et al, Biochemistry, Benjamin/Cummings Publ, 1990, pp 126–128, 826–827.*
Carey F, Organic Chemistry, 2nd Ed., McGraw Hill, 1992, pp. 73–75, 692–693, 927–929, 1122–1124.*
Stryer, Lubert, Biochemistry, 3rd ed., W.H. Freeman & Co., NY, Jan. 1988, pp 117–123.*
Mathews, C.K., et al., Biochemistry, Benjamin/Cummings Publishing Co., Jan. 1990, pp 126–128, 826–827.*
Carey, Francis, Organic Chemistry, 2nd Ed., McGraw Hill, Jan. 1992, pp.*
Li, S., et al, Elimination of band compression in sequencing gels by the use of N4–methyl–2'–deoxycytidine 5'–triphosphate, Nucleic Acids Research, Jun. 1993, vol. 21, No. 11, pp 2709–2714.*
Seela, F., Thomas, H., Duplex Stabilization of DNA: Oligonucleotides Containing 7–Substituted 7–Deazaadenines, Helvetica Chimica Acta, Feb. 22, 1995, vol. 78, pp. 94–108.*
Buhr et al., "Oligodeoxynucleotides containing C–7 Propyne Analogs of 7–deaza–2'–deoxyguanosine and 7–deaza–2'–deoxyadenosine," Nucl. Acids Res. 24:2974–2980 (1996).

Gough, J. A. et al., "Sequence diversity among related genes for recognition of specific targets in DNA molecules," J. Mol. Biol. 166:1–19 (1983).
Innis, M. A. et al., "DNA sequencing with Thermus aquaticus DNA polymerase and direct seqencing of polymerase chain reaction–amplified DNA," Proc. Natl. Acad. Sci. USA 85:9436–9440 (1988).
Li, S. et al., "Elimination of band compression in sequencing gels by the use of $N^4$–methyl–2'–deoxycytidine 5'–triphosphate," Nucl. Acids Res. 21(11):2709–2714 (1993).
Maxam, A. M. et al., "[57]Sequencing end–labeled DNA with base–specific chemical cleavages," Methods–Enzymol. 65(1):499–560 (1980).
Mizusawa, S. et al., "Improvement of the dideoxy chain termination method of DNA sequencing by use of deoxy–7–deazaguanosine triphosophate in place of dGTP," Nucl. Acids Res. 14(3):1319–1324 (1986).
Mizusawa, S. et al., "Improvement of the dideoxy chain termination method of DNA sequencing by use of deoxy–7–deazaguanosine triphosphate in place of dGTP," Nucl. Acids Res. 14(3):1319–1324 (1986).
Okada N. et al., "Structure determination of a nucleoside Q precursor isolated from E. coli tRNA: 7–(aminomethyl)–7–deazaguanosine," Nucl. Acids Res. 5:2289–2297 (1978).
Okamoto, K. et al., Chemical Abstract No. 106:176807 & JP61229897A2 (Nippon Zoki) Oct. 14, 1986.
Ramzaeva et al., "123. 7–Deazaguanine DNA: Oligonucleotides with Hydrophobic or Cationic Side Chains," Helvetic Chimica Acta 80:1809–1822 (1997).
Ramzaeva et al., ".88. 7–Substituted 7–Deaza–2'–deoxyguanosines: Regioselective Halogenation of Pyrrolo [2,3–d] pyrimidine Nucleosides," Helvetica Chimica Acta 78:1083–1091 (1995).
Sanger, F. et al., "DNA sequencing with chain–terminating inhibitors," Proc. Natl. Acad. Sci. USA 74(12):5463–5467 (1977).
Sood, A. et al., "Boron–containing nucleic acids. 2. Synthesis of oligodeoxynucleoside boranophosphates," J. Am. Chem. Soc. 112:9000–9001 (1990).
Tabor, S. et al., "A single residue in DNA polymerase of the Escherichia coli DNA polymerases I family is critical for distinguishing between–deoxy and dideoxyribonucleotides," Proc. Natl. Acad. Sci. USA 92:6339–6343 (1995).
Tabor, S. et al., "DNA sequence analysis with a modified bacteriophage T7 DNA polymerase," Proc. Natl. Acad. Sci. USA 84:4767–4771(1987).
Tomasz, J. et al., "5'–P–borane–substituted thymidine monophosphate and triphosphate," Angew. Chem. Int. Ed. Engl. 31(10):1373–1375 (1992).
Winkeler, H. D. et al., "Synthesis of 2–amino–7–(2' deoxy–β–D–erythro–pentofuranosyl)– 3, 7–dihydro–4H–pyrrolo [2,3–d]pyrimidin–4–one, a new isostere of 2'deoxyguanosine," J. Org. Chem. 48:3119–3122 (1983).

* cited by examiner

Primary Examiner—Marjorie Moran
(74) Attorney, Agent, or Firm—Foley & Lardner LLP

(57) ABSTRACT

Derivatives of 7-deaza-2'-deoxyguanosine are described. Also described is the use of such compounds in synthesis of nucleic acid polymers and in methods for determining a nucleotide base sequence.

20 Claims, 3 Drawing Sheets

DERIVATIVES OF 7-DEAZA -2'-DEOXYGUANOSINE-5'-TRIPHOSPHATE, PREPARATION AND USE THEREOF

RELATED APPLICATION

This application claims benefit of U.S. patent application Ser. No. 60/041,320, filed Mar. 20, 1997, entitled "DERIVATIVES OF 7-DEAZA-2'-DEOXYGUANOSINE-5'-TRIPHOSPHATE, PREPARATION AND USE THEREOF" by Carl W. Fuller et al., which is hereby incorporated by reference herein in its entirety including any figures.

FIELD OF THE INVENTION

The present invention relates to derivatives of 7-deaza-2'-deoxyguanosine-5'-triphosphate (7-deaza-dGTP), their preparation and their use in biological processes, particularly in sequencing.

BACKGROUND OF THE INVENTION

The following is a discussion of the relevant art, none of which is admitted to be prior art to the appended claims.

Winkler et al. (J. Org. Chem 1983, 48: 3119–3122) disclose the compound 7-deaza-2'-deoxyguanosine.

U.S. Pat. Nos. 4,804,748 and 5,480,980 disclose that 7-deaza-dG derivatives of the family (I):

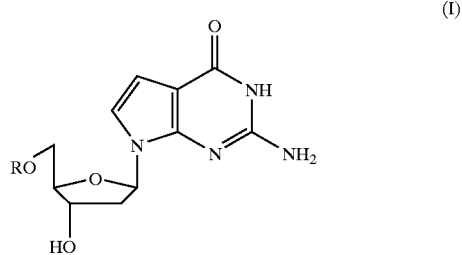

wherein R is $PO_3H_2$, $P_2O_6H_3$, $P_3O_9H_4$ or an alkali metal, alkaline earth metal, or ammonium salt of the phosphate groups; are useful in sequencing in that they provide good gel electrophoretic separation of guanosine, cytosine-rich sequence fragments which can otherwise be difficult to resolve.

The final analysis step in DNA sequencing, whether done using chain-termination (Proc. Natl. Acad. Sci. U.S.A.; 1977; 74(12): 5463–7 "Sanger sequencing") or chain-cleavage (Methods-Enzymol.; 1980; 65(1): 499–560) methods, involves the use of a denaturing polyacrylamide electrophoresis gel to separate DNA molecules by size.

Electrophoretic separation based solely on size requires complete elimination of secondary structure from the DNA. This is typically accomplished by using high concentrations of urea in the polyacrylamide matrix and running the gels at elevated temperatures. For most DNAs, this is sufficient to give a regularly spaced pattern of "bands" in a sequencing experiment. Exceptions can occur if the sequence has a dyad symmetry that can form a stable "stem-loop" structure (Proc. Natl. Acad. Sci. U.S.A.; 1987; 84(14): 4767–71). When these sequences are analyzed by gel electrophoresis, some bases may not be completely resolved. The bands representing different bases run at nearly the same position on the gel, "compressed" tightly together, with bands appearing in two or three lanes at the same position. The bases just above the compressed ones are spaced farther apart than normal as well.

Compression artifacts are caused whenever stable secondary structures exist in the DNA under the conditions prevailing in the gel matrix during electrophoresis. The folded structure apparently runs faster through the gel matrix than an equivalent unfolded DNA, catching up with the smaller DNAs in the sequence. Typical gel conditions (7M urea and 50° C.) denature most secondary structures, but not all structures, particularly those with 3 or more G-C base pairs in succession.

Some gel compression artifacts can be eliminated by using an analog of dGTP during synthesis. The use of nucleotide analogs dITP (J. Mol. Biol. 1983; 166: 1–19), 7-deaza-dGTP (Nucleic Acids Res. 1986; 14(3): 1319–24) and 4-aminomethyl dCTP (Nucleic-Acids Res. 1993; 21(11): 2709–14) for dideoxy sequencing have been described. When dITP or 7-deaza-dGTP replace dGTP in the sequencing experiment, the dG nucleotides in the product DNA are replaced by dI or 7-deaza-dG. These form weaker base-pairs with dC, which are more readily denatured for gel electrophoresis. A comparison of the three sequences in FIG. 5 of Proc. Natl. Acad. Sci. U.S.A. 1987; 84(14): 4767–71 shows that dI fully disrupts secondary structure while 7-deaza-dG only partially resolves this relatively strong compression sequence.

None of these substitute nucleotides is adequate for all sequencing situations. For example: 4-aminomethyl dCTP fails to work well with Sequenase DNA polymerase (Nucleic Acids Res. 1993, 21(11): 2709–14); it is difficult to use dITP for sequencing when using thermostable polymerases such as Taq DNA polymerase (Proc. Natl. Acad. Sci. U.S.A. 1988; 85(24): 9436–40); and 7-deaza-dGTP does not resolve all compression sequences (Proc. Natl. Acad. Sci. U.S.A. 1987; 84(14): 4767–71).

SUMMARY OF THE INVENTION

The present invention provides derivatives of 7-deaza-dGTP which are useful in a number of biological processes, including the resolution of compression artifacts in DNA sequencing. The invention also concerns the preparation of these 7-deaza-dGTP derivatives.

Accordingly, the present invention provides a compound of the formula (II):

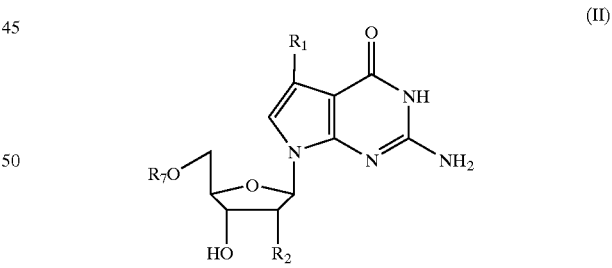

wherein $R_1$ is a $C_{1-10}$ alkyl group optionally substituted by hydroxy, amino, $C_{1-4}$ alkyl substituted amino, $C_{1-4}$ alkoxy or halo; $R_2$ is hydrogen or hydroxy; and $R_7$ is H or a mono-, di- or tri-phosphate or thiophosphate thereof, except that when $R_1$ is methyl $R_7$ is not H.

Thiophosphates are those in which one or more phosphate groups are replaced by a thiophosphate group (e.g. as a tri-thiophosphate, a mono-phosphate-di-thiophosphate or a di-phosphate-mono-thiophosphate). When the compounds of the invention are present as thiophosphates preferably only one group is replaced by a thiophosphate group, normally the α-phosphate group. Preferably the phosphate or thiophosphate group is attached to the C-5 position of the sugar. Similarly, boranophosphates are those in which one or more phosphate groups are replaced by a boranophosphate group (J. Am. Chem. Soc. 1990, 9000–9001; Tomasz et al., Angewandte Chemie. int. Ed. 1992, 31:1373).

By halo is meant fluoro, chloro, bromo or iodo, suitably fluoro or chloro and preferably fluoro.

Suitably $R_1$ is a $C_{1-10}$ alkyl group or a $C_{1-10}$ hydroxyalkyl group, most suitably a $C_{2-6}$ alkyl or $C_{1-5}$ hydroxyalkyl group. Preferably $R_1$ is isopropyl, ethyl or hydroxymethyl. Preferably the compounds of the formula (II) are present as the triphosphates.

The compounds of the formula (II) may be present as salts of the phosphate groups. Suitable salts include alkali metal salts, e.g. lithium, sodium and potassium salts, alkaline earth metal salts, e.g. magnesium and calcium salts, and ammonium salts, e.g. unsubstituted ammonium ions or those that are substituted by $C_{1-4}$ alkyl groups or benzyl or phenethyl groups.

In a further aspect, the present invention provides a nucleotide sequence, one of the nucleotides being a compound of the formula (II). Such a nucleotide sequence can be an oligonucleotide sequence or a polynucleotide sequence. The compound of the formula (II) will either be interspersed between other nucleotides in the chain or be at a terminus of the chain.

Thus, a nucleic acid sequence may have incorporated therein a compound of the formula

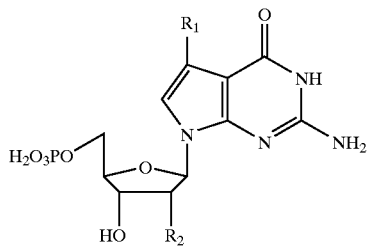

wherein $R_1$ and $R_2$ are as hereinbefore defined.

A nucleic acid sequence having a terminal nucleotide derived from a nucleotide

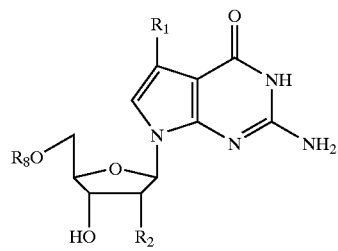

wherein $R_1$ and $R_2$ are as hereinbefore defined and $R_8$ is $P_2O_6H_3$ or $P_3O_9H_4$, also forms part of the present invention.

In a still further aspect, the present invention provides the use of a compound of the formula (II) in the elongation of an oligonucleotide sequence. Such sequence elongation will be carried out in the presence of a DNA polymerase, for example, Taq polymerase or a derivative thereof in which the phenylalanine equivalent to that at position 667 of Taq has been replaced by tyrosine (Proc. Natl. Acad. Sci. U.S.A. 1995 92, 6339–6343), together with one or more other nucleotides necessary to enable sequence elongation.

The triphosphates of the formula (II) can be used instead of 2'-deoxyguanosine-5'-triphosphate in those sequencing methods for DNA in which the use of a DNA polymerase is necessary. Such sequencing methods include Sanger sequencing wherein the sequence is detected by the use of a label, which may be a radiolabel or provided by using dye primers, dye-labeled nucleotides or dye terminators. Preferably the use of the compound of the formula (II) is in sequencing.

Thus, in a preferred embodiment, the present invention provides the use of a compound of the formula (II) in the sequencing of nucleic acids.

The compounds of the formula (II) may be prepared by methods analogous to those known in the art, for example those compounds which are mono-, di- and tri-phosphates may be prepared from the corresponding hydroxy compounds by phosphorylation with a phosphorylation agent, for example, for monophophates phosphorous oxychloride, in a trialkyl phosphate, such as trimethyl phosphate, as solvent. Suitably, phosphorylation is carried out at a non-extreme temperature, e.g. −20° to 30° C. and preferably −10° to 10° C.

Di- and tri-phosphates may be prepared from the monophosphates by activating a salt of this, such as a trialkylammonium salt, and subsequently condensing a trialkylammonium phosphate or diphosphate, e.g. tributylammonium phosphate or diphosphate in a suitable solvent, e.g. an anhydrous dipolar aprotic solvent such as dimethylformamide at a non-extreme temperature, e.g. −20° to 20° and preferably −10° to 10° C., optionally in the presence of a condensation promoting agent and/or a base.

The compounds of the formula (II) wherein $R_1$ is alkyl other than methyl may be prepared by (i) the reduction of the corresponding compound of the formula (III):

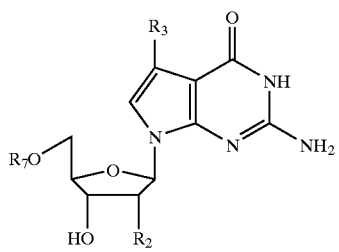

(III)

or a mono, di- or triphosphate or thiophosphate thereof wherein $R_2$ is as hereinbefore defined and $R_3$ is the corresponding alkynyl compound. Such reduction is conveniently carried out by hydrogenation in the presence of a catalyst, e.g. a transition metal catalyst such as palladium in a suitable solvent, e.g. an $C_{1-6}$ alkanol or aqueous $C_{1-6}$ alkanol, such as aqueous methanol, at a non-extreme temperature, for example, 1–10° to 100° C., and conveniently at room temperature, optionally under pressure, e.g. 20 to 40 psig of hydrogen.

The alkynyl compounds may be prepared as described in the literature, e.g. see Nucleic Acid Research (1996) 24: 2974–2980.

The compounds of the formula (II) may also be prepared by the deprotection of a compound of the formula (IV)

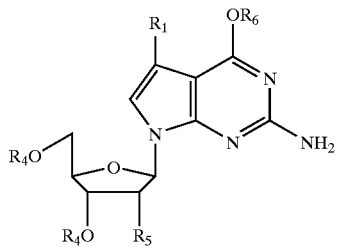

(IV)

wherein $R_1$ is as herebefore defined, $R_4$ is a protecting group, $R_5$ is hydrogen or a group $OR_4$, and $R_6$ is a protecting group which may be the same or different from $R_4$.

The protecting groups are groups that can be removed without affecting other parts of the molecule. Thus, for example, if $R_6$ is a different protecting group from $R_5$, then it may be possible to selectively deprotect one group but retain the other. Suitable protecting groups include $C_{1-6}$ alkyl groups, such as methyl, benzoyl optionally substituted by one to three methyl or ethyl groups, e.g. toluoyl and phenyl substituted methyl or ethyl groups, such as benzyl. Alternatively, the $R_4$ groups may be linked, for example, to form a tetraisopropyldisiloxane group. Compounds of the formula (IV) in which $R_1$ is other than alkyl, e.g. a group $R_{1a}$ may be prepared by the reaction of the corresponding compound, where $R_1$ is a halo group with a derivative of $R_{1a}$, such that $R_{1a}$ is attached to the deazapurine ring, or a derivative of $R_{1a}$ is attached to the deazapurine ring which may be converted to $R_{1a}$.

The protecting groups are removed by conventional techniques, e.g. base, hydrogenation, or use of a Lewis acid such as aluminum chloride.

The compound of the formula (IV) may be prepared by glycosylation of a compound of the formula (V)

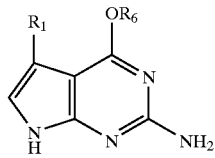

(V)

with a compound of the formula (VI):

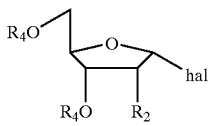

(VI)

wherein $R_1$, $R_2$, $R_4$ and $R_6$ are as hereinbefore defined, and hal is halo, e.g. chloro, bromo or iodo, preferably chloro.

Novel intermediates of the formulae (III) and (IV) also form part of the present invention, such novel intermediates include the phosphates of the alkyl and alkynyl compounds. Triphosphates of the compounds of the formula (III) are particularly preferred.

Other features and advantages of the invention will be apparent from the following description of the preferred embodiments thereof, and from the claims.

DESCRIPTION OF THE PREFERRED EMBODIMENTS

Figure 1:
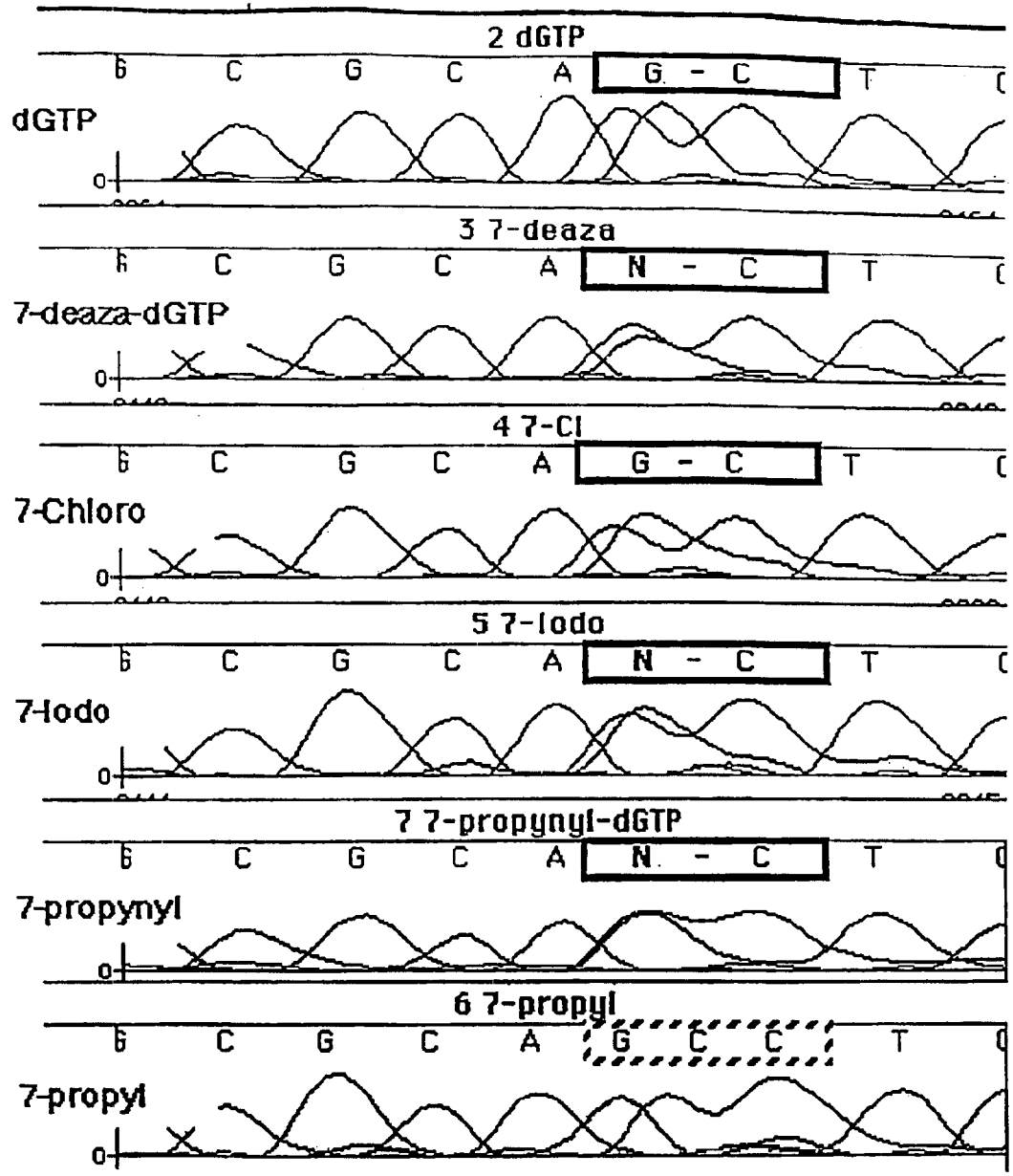
FIG. 1 presents DNA sequence data generated from a region approximately 235 bases from the priming site of pGEM3Zf+ (Promega) using dGTP or an analog of dGTP in the sequencing reaction.

The following Examples are provided for further illustrating various aspects and embodiments of the present invention and are in no way intended to be limiting of the scope.

The present examples illustrate the preparation of the compounds of the present invention and their properties.

EXAMPLE 1

7-propyl-7-deaza-2'-deoxyguanosine-5'-triphosphate a) 7-(Prop-1-ynyl)-7-Deaza-2'-Deoxyguanosine-5'-Triphosphate.

To 200 mg (0.66 mmol) of 7-(prop-1-ynyl)-7-deaza-2'-deoxyguanosine (Nucleic Acid Research (1996) 24: 2974–2980) in a 50 ml round bottom flask under argon was added 5 ml of trimethylphosphate. The reaction mixture was cooled via an ice bath and 74 μl (0.79 mmol, 1.2 eq.) of phosphorus oxychloride (redistilled) was added. The reaction was stirred with cooling for two hours. Both 1 M tributylammonium pyrophosphate in anhydrous DMF (3.3 ml, 3.3 mmol, 5 eq.) and tributylamine (0.8 ml, 3.3 mmol, 5 eq.) were then added slowly to the cooled solution, simultaneously. After addition, the reaction mixture was stirred for 10 minutes. At this point, cooled 1 M triethylammonium bicarbonate buffer (TEAB, pH=7.0) was added to a final volume of 40 ml and the mixture was stirred overnight at room temperature. The next day, the solution was evaporated under high vacuum to a viscous solution. The crude product was then applied to a 200 ml Sephadex A25 column which was eluted with 0.05 M to 1 M TEAB (pH=7.0) at a flow rate of 1.2 ml per minute. A peak containing the product was collected at approximately 0.9 M. After evaporation, the triphosphate was finally purified on a reverse phase D PAK C 18 HPLC column (5 by 30 cm) using a 0% B to 100% B gradient in 45 minutes at 130 ml per minute (A=0.1 M TEAB, pH=7.0 and B=25% acetonitrile in 0.1 M TEAB, pH=7.0). $^{31}$P NMR: −5.96 (d); −10.60 (d); −21.98 (t). HPLC (D PAK C 18, 3.9 by 30 cm, 0% B to 100% B in 30 minutes at 1 ml per minute) 20.5 minutes. UV (pH 7.0) 237 nm (max), 273 nm, and 295 nm.

b) 7-Propyl-7-Deaza-2'-Deoxyguanosine-5'-Triphosphate.

To 50 mg of the triethlyammonium salt of 7-(prop-1-ynyl)-7-deaza-2'-deoxyguanosine-5'-triphosphate was added 10 ml of 10% aqueous methanol. This solution was transferred to a glass pressure vessel. The vessel was then purged with argon and 20 mg of 10% palladium on carbon was added. The pressure vessel was then placed into the shaker arm of the hydrogenation apparatus and charged with 30 psig of hydrogen. The reaction mixture was shaken for 2 hours. After the hydrogen was discharged, the solution was passed through a small plug of Celite. The plug was washed with 10% aqueous methanol. The combined solution was then evaporated to dryness. The product was purified on a reverse phase D PAK C 18 HPLC column (5 by 30 cm) using a 0% B to 100% B gradient in 45 minutes at 130 ml per minute (A=0.1 M TEAB, pH=7.0 and B=25% acetonitrile in 0.1 M TEAB, pH=7.0). $^{31}$P NMR: −9.98 (d); −10.60 (d); −22.41 (t). HPLC (D PAK C 18, 3.9 by 30 cm, 0% B to 100% B in 30 minutes at 1 ml per minute) 22.3 minutes. UV(pH 7.0) 225 nm (max), 259 nm (sh), and 286 nm.

EXAMPLE 2

7-Hexynyl- and 7-Hexyl-7-Deaza-2'-Deoxyguanosine-5-Triphosphate

7-Hexynyl-7-deaza-2'-Deoxyguanosine-5'-triphosphate was prepared in an analogous manner starting with 7-Hexynyl-7-deaza-2'-Deoxyguanosine (Helvetica Chimica Acta (1995) 78:1083–1090). $^{31}$P NMR: −5.98 (d); −10.59 (d); −21.79 (bm). HPLC (D PAK C 18, 3.9 by 30 cm, 0% B to 50% B in 30 minutes at 1 ml per minute) 19.4 minutes. UV (pH 7.0) 238 nm (max), 273 nm, and 295 nm. Reduction by hydrogen in an analogous manner yielded 7-Hexyl-7-Deaza-2'-Deoxyguanosine-5'-Triphosphate. $^{31}$P NMR: −8.73 (d); −10.43 (d); −22.12 (t). HPLC (D PAK C 18, 3.9 by 30 cm, 0% B to 50% B in 30 minutes at 1 ml per minute) 21 minutes. UV (pH 7.0) 225 nm (max), 265 nm (sh), and 285 nm.

EXAMPLE 3

7-Hydroxymethyl-7-Deaza-2'-Deoxyguanosine-5'-Triphosphate

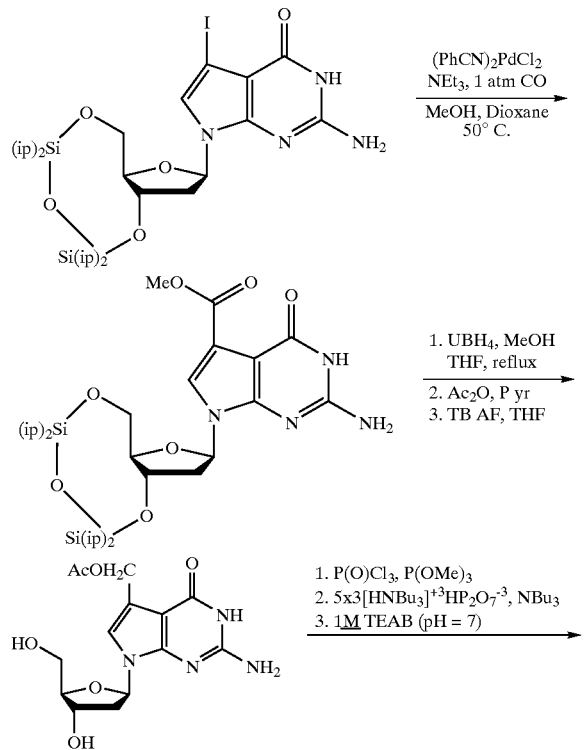

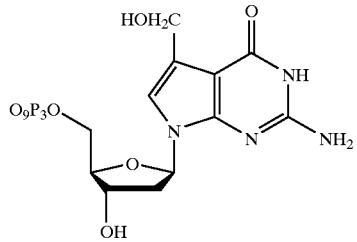

a) 2'-deoxy-3',5'-O-(tetraisopropyldisiloxane-1,3-diyl)-7-carbomethoxy-7-deazaguanosine:

To a 250 ml round bottom flask under argon positive pressure was charged 1.15 gm (1.87 mmol) 2'-deoxy-3',5'-O-(tetraisopropyldisiloxane-1,3-diyl)-7-iodo-7-deazaguanosine, 9 mg (0.023 mmol) bis(benzonitrile) dichloropalladium (II), 288 μl (3.6 mmol) triethylamine, 30 ml methanol, and 30 ml dioxane. The reaction mixture was purged with carbon monoxide gas for 5 minutes and allowed to remain under CO positive pressure (by use of a CO filled balloon). The magnetically stirred solution was heated to 50° C. overnight. After cooling 9 mg bis(benzonitrile) dichloropalladium (II) and 288 μl (3.6 mmol) triethylamine were added to the reaction mixture and the reaction was heated for an additional 18 hours under CO pressure. At this point, the reaction mixture was cooled and solvent removed by evaporation. The residue was then purified by silica gel 60 column chromatography using 0% to 10% methanol in chloroform to elute the product. A yield of 0.48 gm (47%) of the title compound was obtained. $^1$H NMR (ppm in CDCl$_3$): 10.83 (NH, bs), 7.52 (H-8, s), 6.48 (NH$_2$, bs), 6.27 (H-1', d), 4.66 (H-3', q), 4.03 (H-5', bs), 3.81 (H-4', m), 3.73 (CH$_3$O s), 2.49 (H-2', m), 2.05 (H-2', m), 1.05 (4×Si—CH(CH$_3$)$_2$, bd). $^{13}$C NMR (ppm in CDCl$_3$): 163.48 (CO), 159.34 (C$_6$), 153.69 (C$_2$), 152.67 (C$_4$), 124.84 (C$_8$), 110.31 (C$_5$), 98.38 (C$_7$), 84.82 (C$_{4'}$), 82.23 (C$_{1'}$), 69.45 (C$_{3'}$), 61.50 (C$_{5'}$) 51.02 (CH$_3$O), 40.16 (CH$_{2'}$), 17.4 to 12.45 (4×Si—CH(CH$_3$)$_2$, 10 peaks). IR (cm−1, mineral oil): 1713 (CO stretch).

b) 2'-deoxy-3',5'-O-(tetraisopropyldisiloxane-1,3-diyl)-7-hydroxymethyl-7-deazaguanosine:

To a 25 ml two-neck round bottom flask fitted with a reflux condenser under argon positive pressure was added 370 mg (0.68 mmol) 2'-deoxy-3',5'-O-(tetraisopropyldisiloxane-1,3-diyl)-7-carbomethoxy-7-deazaguanosine, 59 mg (2.7 mmol) lithium borohydride, and 10 ml anhydrous tetrahydrofuran. The reaction mixture was brought to reflux and 110 μl (2.7 mmol) methanol was added dropwise via a syringe. Heating continued for an additional half an hour after this addition. The reaction mixture was then cooled and a few drops of water were added, followed by a few drops of 1N HCl; no further gas evolution was observed with the last drop. The reaction mixture was then filtered through a plug of celite, and the celite washed with ethyl acetate and methanol. The combined organic fraction was evaporated and the residue applied to a silica gel 60 column chromatography. Ethyl acetate was used to elute the product. A yield of 0.27 gm (76%) of the title compound was obtained. $^1$H NMR (ppm in CDCl$_3$): 7.23 (8-H, s), 6.65 (NH$_2$, s), 6.26 (H-1', dd), 5.03 (CH$_2$OH, s), 4.62 (H-3', m), 3.95 (H-5', dq), 3.78 (H-4', m), 2.43 (H-2', m), 1.02 (4×Si—CH(CH$_3$)$_2$, m).

c) 2'-deoxy-3',5'-O-(tetraisopropyldisiloxane-1,3-diyl)-7-o-acetoxymethyl-7-deazaguanosine:

To a 25 ml round bottom flask was charged 260 mg (0.5 mmol) 2'-deoxy-3',5'-O-(tetraisopropyldisiloxane-1,3-diyl)-7-hydroxymethyl-7-deazaguanosine in 10 ml anhydrous pyridine. To the magnetically stirring mixture was added 71 μl (0.75 mmol) acetic anhydride dropwise via syringe. The reaction mixture was stirred for 12 hours. At this point 5 ml methanol was added and the mixture stirred for an additional one half hour. This was followed by evaporation of the solvents. The residue was redissolved in ethyl acetate and washed with 2 times water and one times saturated aqueous sodium bicarbonate. The organic fraction was dried with sodium sulfate, filtered and evaporation of ethyl acetate yielded 0.254 gm (91%) of the product.

d) 2'-deoxy-7-o-acetoxymethyl-7-deazaguanosine:

To a 25 ml round bottom flask was charged 254 mg (0.45 mmol) 2'-deoxy-3',5'-O-(tetraisopropyldisiloxane-1,3-diyl)-7-o-acetoxymethyl-7-deazaguanosine in 5 ml anhydrous THF. To this magnetically stirred mixture was added 1.8 ml 1 M tetrabutylammonium fluoride in THF and the reaction was stirred for one hour. At this point, the solution was evaporated and the residue was purified by silica gel 60 column chromatography. The pure product was obtained by elution with 0% to 10% methanol in chloroform. A yield of 0.13 gm (85%) 2'-deoxy-7-o-acetoxymethyl-7-deazaguanosine was obtained. $^1$H NMR (ppm in d$^6$-DMSO): 10.42 (NH, s), 6.99 (8-H, s), 6.30 (NH$_2$, bs), 6.30 (H-1', m), 5.05 (CH$_2$OAc, s), 4.24 (H-3', m), 3.73 (H-4', m), 3.44 (H-5', m), 2.27 (H-2', m), 2.04 (H-2', m), 2.00 (CH$_3$CO, s).

e) 7-hydroxyethyl-7-deaza-2'-deoxyguanosine-5'-triphosphate:

To 130 mg (0.38 mmol) of 2'-deoxy-7-o-acetoxymethyl-7-deazaguanosine in a 50 ml round bottom flask under argon was added 5 ml of trimethylphosphate. The reaction mixture was cooled via an ice bath and 53 μl (0.57 mmol, 1.5 eq.) of Phosphorus Oxychloride (redistilled) was added. The reaction was stirred with cooling for two hours. Both 1 M Tributylammonium Pyrophosphate in anhydrous DMF (1.9 ml, 1.9 mmol, 5 eq.) and Tributylamine (0.5 ml, 1.9 mmol, 5 eq.) were then added slowly to the cooled solution, simultaneously. After addition, the reaction mixture was stirred for 10 minutes. At this point, cooled 1 M Triethylammonium Bicarbonate buffer (TEAB, pH=7.0) was added to a final volume of 40 ml and the mixture was stirred overnight at room temperature. The next day, the solution was evaporated under high vacuum to an viscous solution. The crude product was then applied to a 200 ml Sephadex A25 column which was eluted with 0.05 M to 1 M TEAB (pH=7.0) at a flow rate of 1.2 ml per minute. The triphosphate peak was collected and purified on a reverse phase D PAK C 18 HPLC column (5 by 30 cm) using a 0% B to 100% B gradient in 45 minutes at 130 ml per minute (A=0.1 M TEAB, pH=7.0 and B=25% Acetonitrile in 0.1 M TEAB, pH=7.0). The purified compound was treated with approximately 10% ammonium hydroxide at 0° C. for 2 hours. The HPLC of this reaction mixture was exactly the same as the starting material, which indicated that the acetyl group had been deprotected during phosphorylation and purification. $^{31}$P NMR: –5.76 (d); –10.47 (d); –21.93 (t). HPLC (D PAK C 18, 3.9 by 30 cm, 0% B to 100% B in 30 minutes at 1 ml per minute) 17.71 minutes. UV(vis) 261 nm (max).

EXAMPLE 4

7-Ethyl-7-Deaza-2'-Deoxyguanosine-5'-Triphosphate and 7-Isopropyl-7-Deaza-2'-Deoxyguanosine-5'-Triphosphate

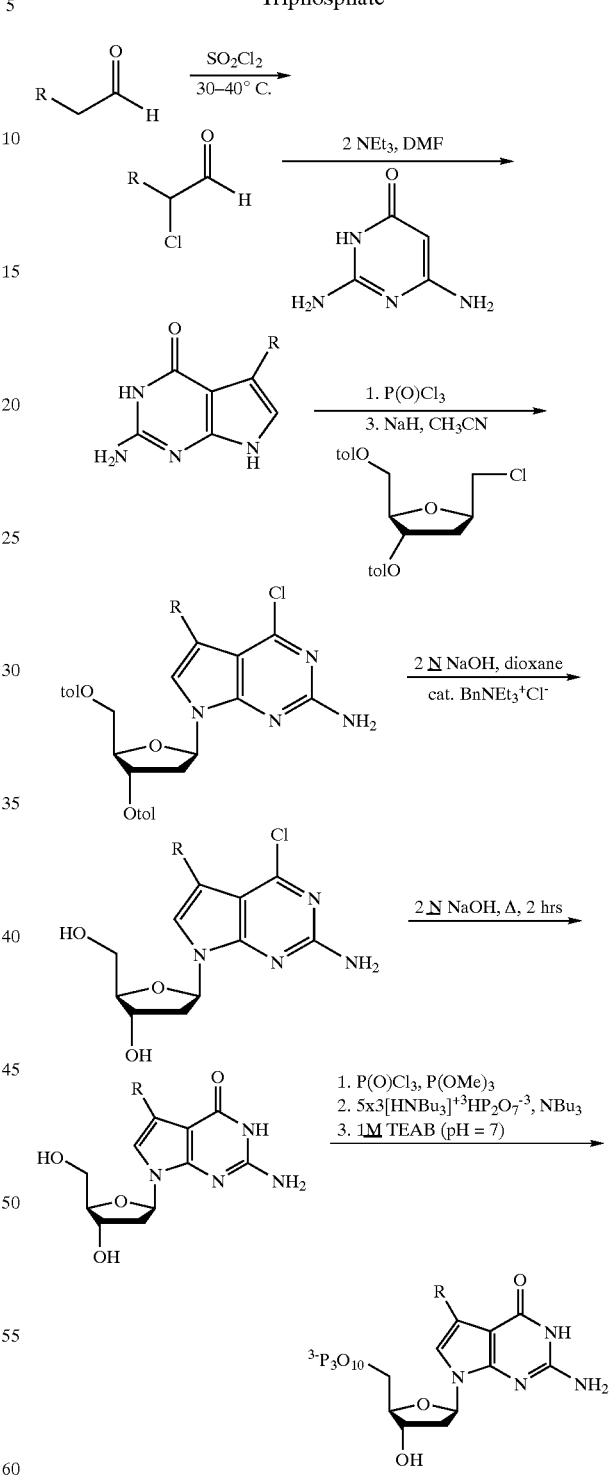

a) 2-chloro-butanal:

To a pre-dried 500 ml 3-neck flask, fitted with a 60 ml addition funnel, a reflux condenser, an internal thermometer, and a magnetic stirring bar, under argon positive pressure was charged 45 ml (0.5 mole) of butanal. The addition funnel was then charged with 40 ml (0.5 mole) of sulfuryl chloride and this reagent was added dropwise to the stirring butanal so that the temperature remained between 20–40° C. A water bath was used to control the exothermic reaction. After the addition of sulfuryl chloride was complete, the water bath was removed and the reaction was allowed to come to room temperature for 15 minutes. After this time the water bath was replaced and the reaction mixture was heated to 40–50° C. for 2 hours, then again at room temperature for one hour. The crude product was then fractionally distilled at approximately 80 mm torr (water aspirator); BP=54–58° C. The product was moisture sensitive and needed to be redistilled just before use. $^1$H NMR (ppm in CDCl$_3$): 9.42 (CHO, d), 4.07 (CHCl, dt), 1.90 (CH$_2$, m), 0.998 (CH$_3$, t).

b) 2-chloro-3-methyl-butanal:

As per the procedure for 2-chloro-butanal. BP: (80 mm torr, water aspirator) 76–82° C. $^1$H NMR (ppm in CDCl$_3$): 9.43 (CHO, d), 3.98 (CHCl, m), 2.28 (CHMe$_2$, m), 1.01 (CH$_3$, d), 0.973 (CH$_3$, d).

c) 7-ethyl-7-deazaguanine:

To a 2-neck 100 ml flask, fitted with a 15 ml addition funnel and a magnetic stirring bar, under argon positive pressure was charged 9.86 gm (78.2 mmol) 2,6-diaminopyrimidine, 40 ml anhydrous DMF, and 22 ml (157.8 mmol) triethylamine. Freshly distilled 2-chloro-butanal (8.4 gm, 78.9 mmol) was then added to the stirring suspension dropwise via the addition funnel over a period of 0.5 hours. The exothermic reaction was brought back to room temperature as soon as it began to get hot by means of a water bath. At this point, the solid went into solution. After complete addition of the 2-chloro-butanal the reaction was allowed to stir overnight at room temperature. The solvent was removed at this point and the solid resuspended in 100 ml water. This then was cooled at 5° C. overnight in the refrigerator.

The compound was collected by filtration, washed with water (2×20 ml), ether (2×50 ml), and finally dried in vacuo. A yield of 10.9 gm of product (71%) was obtained. $^1$H NMR (ppm in d$^6$-DMSO): 10.59 (NH, s), 10.17 (NH, s), 6.30 (8-H, s), 5.93 (NH$_2$, s), 2.54 (CH$_2$, q), 1.16 (CH$_3$, t).

d) 7-isopropyl-7-deazaguanine:

As per the procedure for 7-ethyl-7-deazaguanine. Yield=69%. $^1$H NMR (ppm in d$^6$-DMSO): 10.55 (NH, s), 10.05 (NH, s), 6.28 (8-H, s), 5.93 (NH$_2$, bs), 3.01 (CH, m), 1.17 (CH$_3$, d).

e) 2-amino-6-chloro-7-ethyl-7-deazapurine:

To a 1 L round bottom flask fitted with a reflux condenser and magnetic stirring bar under argon positive pressure was charged in order: 16 gm (90 mmol) 7-ethyl-7-deazaguanine, 41 gm (180 mmol) benzyltriethylammonium chloride, 450 ml anhydrous acetonitrile, 16 ml (123 mmol) N,N-dimethylaniline, and 51 ml (540 mmol) phosphorous oxychloride. The reaction mixture was brought to reflux for one hour. The reaction was allowed to cool to room temperature, then acetonitrile and excess phosphorous oxychloride were removed by use of a high vacuum rotary evaporator. The resulting oil was poured onto crushed ice and this slurry stirred for about one hour. The solution was adjusted to pH=2 with diluted ammonium hydroxide (approx. 10%). The resulting yellow solid was then collected by filtration and dried in vacuo overnight. The filtrate was extracted twice with ethyl acetate (2×200 ml). The organic fraction was dried with sodium sulfate, filtered, evaporated and kept aside. The dried solid was extracted with warmed ethyl acetate (50° C., 4×0.5 L) and evaporated. The combined evaporated solid material yielded 10 gm (57%) of product. $^1$H NMR (ppm in d$^6$-DMSO): 11.18 (NH, s), 6.81 (8-H, s), 6.41 (NH$_2$, s), 2.70 (CH$_2$, q), 1.18 (CH$_3$, t).

f) 2-amino-6-chloro-7-isopropyl-7-deazapurine:

As per the procedure for 2-amino-6-chloro-7-ethyl-7-deazapurine. Yield=33%. $^1$H NMR (ppm in d$^6$-DMSO): 11.16 (NH, s), 6.82 (8-H, s), 6.39 (NH$_2$, s), 3.23 (CH, m), 1.14 (CH$_3$, d).

g) 2'-deoxy-3',5'-di-O-(p-toluoyl-β-D-erythro-pentofuranosyl)-2-amino-6-chloro-7-ethyl-7-deazapurine:

To a 250 ml round bottom flask under argon positive pressure was charged 1 gm (5.1 mmol) 2-amino-6-chloro-7-ethyl-7-deazapurine, 0.234 g (5.85 mmol) sodium hydride (60% dispersion in mineral oil), and 100 ml anhydrous acetonitrile. The suspension was magnetically stirred for one hour at which point all the solid had gone into solution turning it light orange. 2-deoxy-3,5-di-O-p-toluoyl-a-D-erythro-pentofuranosyl chloride solid was added to the stirring solution in four portions of 0.543 gm each (2.17 gm, 5.6 mmol total) every fifteen minutes. After the final addition the reaction mixture was allowed to stir for an additional hour. The solvent was then evaporated and the residue purified by silica gel 60 column chromatography. Elution with 10% to 20% ethyl acetate in hexane removed the pentofuranosyl impurities, while further elution with 30% ethyl acetate in hexane yielded the product. A yield of 1.9 gm (69%) was collected. $^1$H NMR (ppm in CDCl$_3$): 7.94 (Ar, t), 7.24 (Ar, t), 6.68 (8-H, s), 6.59 (H-1', –dd), 5.72 (H-3', bm), 4.93 (NH$_2$, s), 4.65 (H-5', ddd), 4.54 (H-4', m), 2.81 (H-2', m), 2.63 (CH$_2$, q), 2.59 (H-2', m), 2.42 (tol-CH$_3$, s), 2.40 (tol-CH$_3$, s), 1.08 (CH$_3$, t).

h) 2'-deoxy-3',5'-di-O-(p-toluoyl-β-D-erythro-pentofuranosyl)-2-amino-6-chloro-7-isopropyl-7-deazapurine:

As per the procedure for 2'-deoxy-3',5'-di-O-(p-toluoyl-β-D-erythro-pentofuranosyl)-2-amino-6-chloro-7-ethyl-7-deazapurine. Yield=65%. $^1$H NMR (ppm in CDCl$_3$): 7.28 (Ar, t), 6.60 (8-H, s), 6.59 (Ar, t), 5.96 (H-1', dd), 5.17 (H-3', bd), 4.40 (NH$_2$, s), 4.04 (H-5', ddd), 3.89 (H-4', bm), 2.63 (CH, m), 3.13 (tol-CH$_3$, s), 3.09 (tol-CH$_3$, s), 2.19 (H-2', m), 1.95 (H-2', m), 1.21 (CH$_3$, d).

i) 2'-deoxy-(β-D-erythro-pentofuranosyl)-2-amino-6-chloro-7-ethyl-7-deazapurine:

A mixture of 2'-deoxy-3',5'-di-O-(p-toluoyl-β-D-erythro-pentofuranosyl)-2-amino-6-chloro-7-ethyl-7-deazapurine (1.25 gm, 2.5 mmol), benzyltriethylammonium chloride (20 mg, 0.1 mmol), 2 N sodium hydroxide (20 ml, 40 mmol), and dioxane (50 ml) was vigorously stirred for 7 hours. After evaporation, the residue was slurried into 10 ml H$_2$O and this solution neutralized to pH=7.0 with 2 N HCl using a pH meter. The suspension was cooled overnight at 5° C. At this point, the solid was filtered, washed with cold H$_2$O, then dried in vacuo. A yield of 0.53 gm (68%) of the title compound was obtained. $^1$H NMR (ppm in d$^6$-DMSO): 7.08 (8-H, s), 6.60 (NH$_2$, bs), 6.42 (H-1', dd), 4.29 (H-3', m), 3.75 (H-4', m), 3.48 (H-5', m), 2.71 (CH$_2$, q), 2.37 (H-2', m), 2.06 (H-2', m), 1.32 (CH$_3$, t).

j) 2'-deoxy-(β-D-erythro-pentofuranosyl)-2-amino-6-chloro-7-isopropyl-7-deazapurine:

As per the procedure for 2'-deoxy-(β-D-erythro-pentofuranosyl)-2-amino-6-chloro-7-ethyl-7-deazapurine. Yield=72%. $^1$H NMR (ppm in d$^6$-DMSO): 6.62 (8-H, s), 6.17 (H-1', dd), 4.49 (NH$_2$, s), 4.78 (H-3', db), 4.12 (H-4', bs), 3.85 (H-5', m), 3.36 (CH, m), 3.03 (H-2', m), 2.17 (H-2', m), 1.24 (CH$_3$, d).

k) 2'-deoxy-7-ethyl-7-deazaguanosine:

A slurry of 0.53 gm (1.8 mmol) 2'-deoxy-(β-D-erythro-pentofuranosyl)-2-amino-6-chloro-7-ethyl-7-deazapurine and 20 ml (40 mmol) 2 N sodium hydroxide was heated to reflux for two hours. During this time all solid went into solution, then precipitated out again. After the reaction time, the solution was cooled to room temperature and neutralized to pH=7.0 with 2 N HCl using a pH meter. This solution was then evaporated and the residue purified by silica gel 60 column chromatography using 5% to 10% methanol in chloroform to elute the product. A yield of 0.34 gm (67%) 2'-deoxy-7-ethyl-7-deazaguanosine was obtained. $^1$H NMR (ppm in d$^6$-DMSO): 10.39 (NH, s), 6.61 (8-H, s), 6.28 (NH$_2$, bs), 6.28 (H-1', dd), 4.26 (H-3', m), 3.73 (H-4', m), 3.48 (H-5', m), 2.57 (CH$_2$, q), 2.29 (H-2', m), 2.03 (H-2', m), 1.16 (CH$_3$, t).

l) 2'-deoxy-7-isopropyl-7-deazaguanosine:

As per the procedure for 2'-deoxy-7-ethyl-7-deazaguanosine. Yield=62%. $^1$H NMR (ppm in d$^6$-DMSO).: 7.96 (NH, s), 6.58 (8-H, s), 6.42 (NH$_2$, bs), 6.27 (H-1', dd), 4.26 (H-3', m), 3.72 (H-4', m), 3.48 (H-5', m), 3.02 (CH, m), 2.31 (H-2', m), 2.01 (H-2', m), 1.20 (CH$_3$, d).

m) 7-ethyl-7-deaza-2'-deoxyguanosine-5'-triphosphate:

As per the preparation and purification for 7-hydroxymethyl-7-deaza-2'-deoxyguanosine-5'-triphosphate. $^{31}$P NMR (ppm in D$_2$O): −10.04 (d); −10.67 (d); −22.59 (t). HPLC (D PAK C 18, 3.9 by 30 cm, 0% B to 100% B in 30 minutes at 1 ml per minute, A=0.1 M TEAB, pH=7.0 and B=25% Acetonitrile in 0.1 M TEAB, pH=7.0) 20.86 minutes. UV(vis) 225 nm (max) and 264 nm.

n) 7-isopropyl-7-deaza-2'-deoxyguanosine-5'-triphosphates:

As per the preparation and purification for 7-hydroxymethyl-7-deaza-2'-deoxyguanosine-5'-triphosphate. $^{31}$P NMR (ppm in D$_2$O): −7.22 (d); −11.42 (d); −22.79 (t). HPLC (D PAK C 18, 3.9 by 30 cm, 0% B to 100% B in 30 minutes at 1 ml per minute, A=0.1 M TEAB, pH=7.0 and B=25% Acetonitrile in 0.1 M TEAB, pH=7.0) 23.02 minutes. UV(vis) 225 nm (max) and 264 nm.

EXAMPLE 5

Other 7-deazadeoxyguanosine compounds

7-Chloro-7-deaza-2'-deoxyguanosine-5'-triphosphate and 7-Iodo-7-deaza-2'-deoxyguanosine-5'-triphosphate were prepared in an analogous manner from 7-Chloro-7-deaza-2'-deoxyguanosine and 7-Iodo-7-deaza-2'-deoxyguanosine (Helvetica Chimica Acta (1995) 78:1083–1090), respectively.

EXAMPLE 6

Use of 7-deaza-dGTP derivatives in sequencing reactions

Sequencing reaction mixtures were prepared as follows:

|  | A Reaction | C Reaction | G Reaction | T Reaction |
|---|---|---|---|---|
| DNA, 200 µg/ml pGEM3Zf4* (Promega) | 1 | 1 | 1 | 1 |
| A-REG Primer* (0.2 µM) | 1 | — | — | — |
| C-FAM Primer (0.2 µM) | — | 1 | — | — |
| G-TKR Primer (0.4 µM) | — | — | 1 | — |
| T-ROX Primer (0.4 µM) | — | — | — | 1 |
| ddA Mix | 1 | — | — | — |
| ddC Mix | — | 1 | — | — |
| ddG Mix | — | — | 1 | — |
| ddT Mix | — | — | — | 1 |
| Buffer 260 mM Tris-HCl pH 9.5, 65 mM MgCl$_2$ | 1 | 1 | 1 | 1 |
| 3.3 units/µl Thermo Sequenase, 0.0055 units/µl pyrophosphatase | 1 | 1 | — | — |
| 6.6 units/µl Thermo Sequenase, 0.011 units/µl pyrophosphatase | — | — | 1 | 1 |
| 940 µM** dGTP or dGTP analog | 1 | 1 | 1 | 1 |

(Volumes in µl)
*Primer is Reverse Energy-Transfer Primer −28 M13 Rev1 (Amersham).
**234 µM for 7-propynyl-7-deaza dGTP The reaction mixtures were placed in a thermal cycler (MJ research) and cycled 30 times at 95° C., 30 sec; 45° C., 15 sec; and 60° C., 4 min. Following the thermal cycling, the samples were pooled, and loaded onto the sequencing instrument as described for sequencing using the Dynamic Direct sequencing kit (Amersham).

Figure 2:
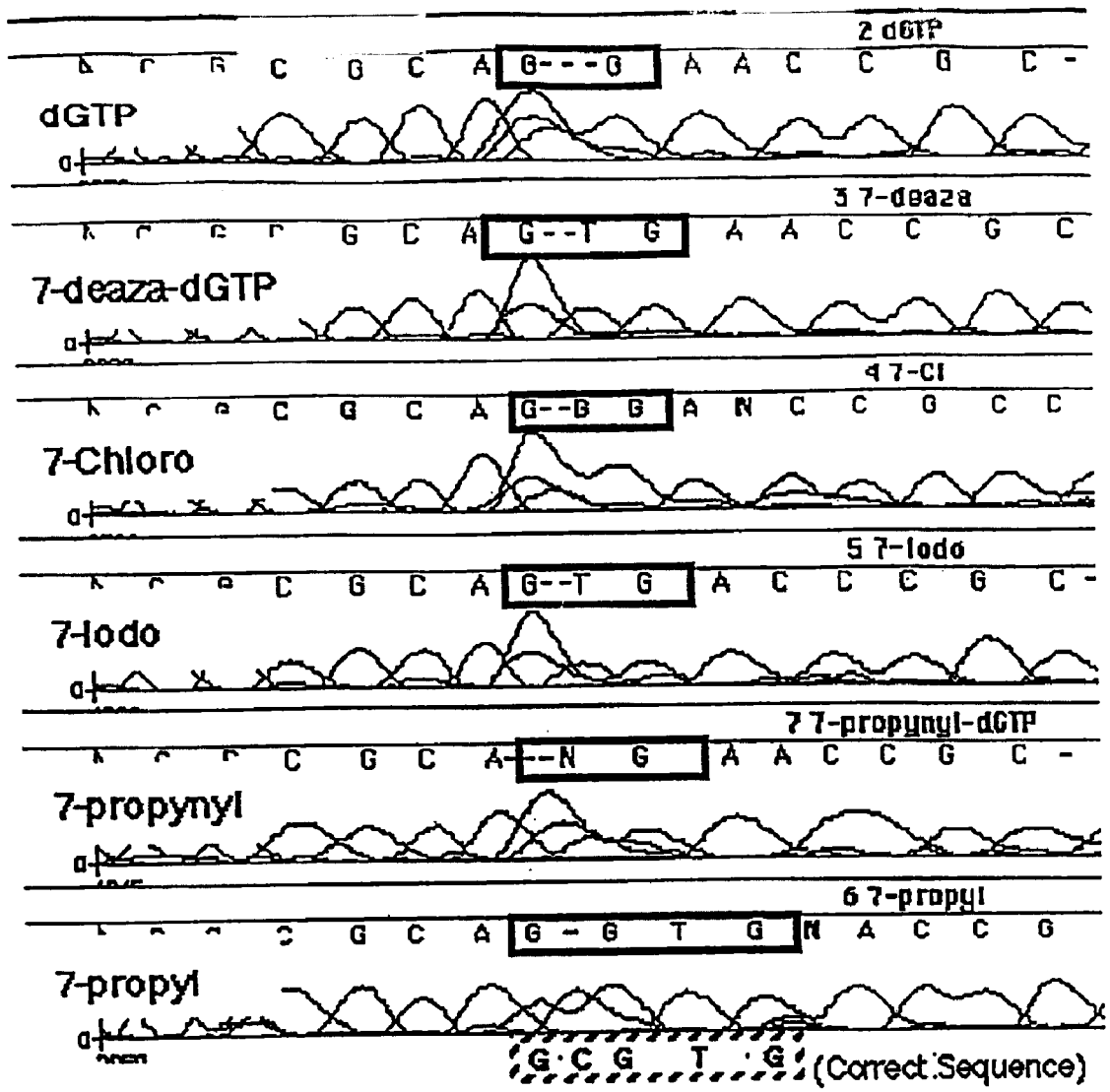
FIG. 2 presents DNA sequence data generated from a region approximately 310 bases from the priming site of pGEM3Zf+ (Promega) using dGTP or an analog of dGTP in the sequencing reaction.

Two regions of interest of the sequence are shown in FIGS. 1 and 2.

A Sequence region approximately 235 bases from the priming site is shown in FIG. 1. The top sequence (run with dGTP) shows a compressed region in which anomalous migration of several bases results in sequence errors (solid box). Of the remaining sequences run with analogs of dGTP, only the bottom one with 7-propyl-7-deaza-dGTP has the correct sequence (broken-line box).

A Sequence region approximately 310 bases from the priming site is shown in FIG. 2. The top sequence (run with dGTP) has a compressed region (solid box). Of the remaining sequences run with analogs of dGTP, none had the correct sequence determined automatically by the software, but the bottom one with 7-propyl-7-deaza-dGTP is the only one which could be edited by simple inspection to the correct sequence (broken-line box).

Figure 3:
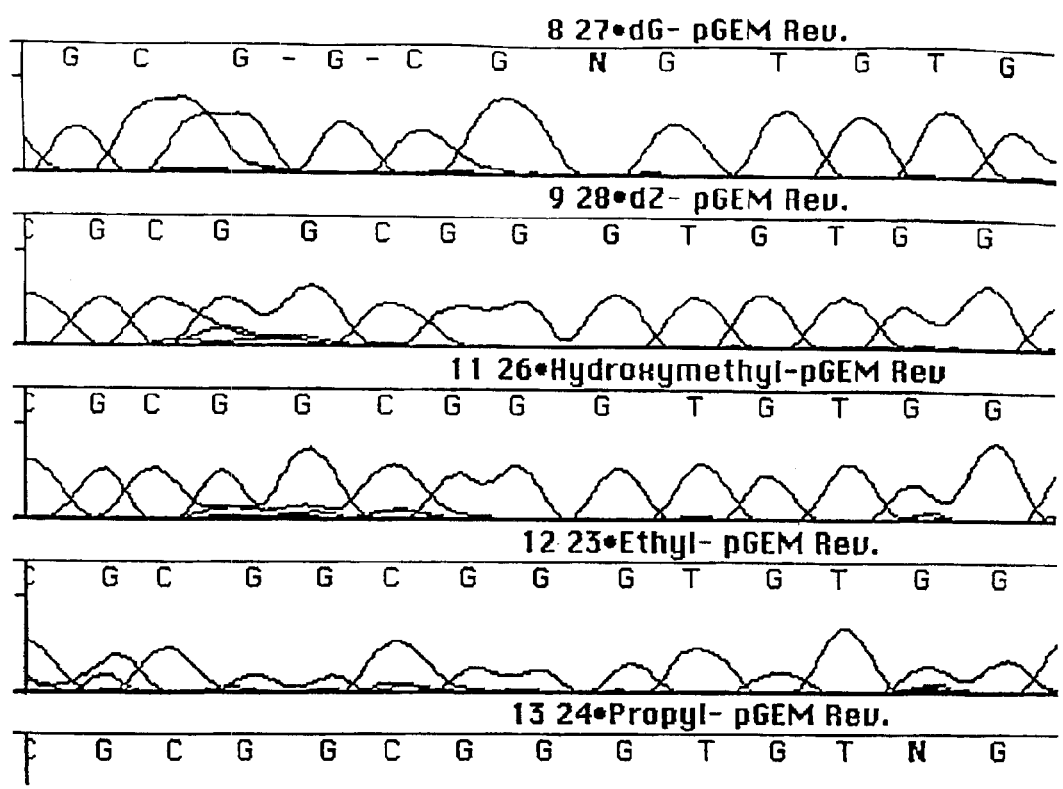
FIG. 3 presents DNA sequence data generated from a region approximately 300 bases from the priming site.

FIG. 3 shows a sequence region approximately 300 bases from the priming site. The top sequence (run with dGTP) has a compressed region. The remaining sequences run with analogs of dGTP, including 7-ethyl-7deaza-dGTP and 7-hydroxymethyl-7-deaza-dGTP, all have the correct sequence.

The accuracies of parallel sequences for a region approximately 129 bases from the priming site to approximately 421 bases from the priming site which had at least 6 regions of compression artifacts were as follows:

| Analog | Errors | % Accuracy |
|---|---|---|
| dGTP | 17 | 94 |
| 7-deaza-dGTP | 5 | 98 |
| 7-Chloro-7-deaza-dGTP | 23 | 92 |
| 7-Iodo-7-deaza-dGTP | 22 | 92 |
| 7-Propynyl-7-deaza-dGTP | 21 | 92 |
| 7-propyl-7-deaza-dGTP | 3 | 99 |

One of the errors in the 7-propyl-7-deaza-dGTP sequence was not related to a compression artifact, and the other two apparent errors are shown in FIG. 2. These two errors could easily be corrected by simple inspection. Thus, this analog gave considerably more accurate sequence with this template than any other analog tested.

Other embodiments are within the following claims.

What is claimed is:

1. Molecule comprising the following moiety:

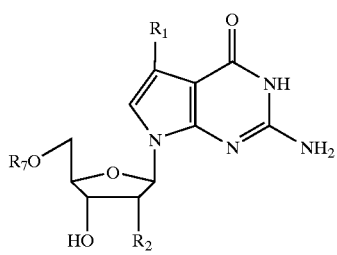

wherein $R_1$ is $C_{1-10}$ alkyl group substituted by hydroxyl, $C_{1-4}$ alkoxy or halo; and $R_2$ is hydrogen and $R_7$ is H or a mono-, di-, tri-phosphate or thiophosphate thereof.

2. The molecule of claim 1, wherein said molecule is a nucleic acid polymer.

3. The molecule of claim 2, wherein said nucleic acid is DNA.

4. A compound of the formula (II):

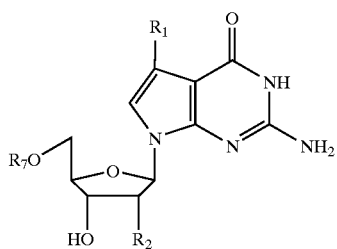

wherein $R_1$ is $C_{1-10}$ to alkyl group substituted by hydroxyl, $C_{1-4}$ alkoxy or halo; $R_2$ is hydrogen; and $R_7$ is H or a mono-, di-, or tri-phosphate or thiophosphate thereof.

5. A compound according to claim 4, wherein $R_1$ is a $C_{2-8}$ alkyl group substituted by hydroxyl, $C_{1-4}$ alkoxy or halo.

6. A compound according to any of the claims 4 or 5 wherein the compound of the formula (II) is present as a triphosphate.

7. A compound of claim 4 wherein $R_7$ is a di-, or tri-phosphate or thiophosphate thereof.

8. A compound of claim 4, wherein said compound is 7-Hydroxymethyl-7-deaza-2'-deoxyguanosine or a mono-, di-, or tri-phosphate thereof.

9. A compound according to any one of claim 8, wherein said compound is a triphosphate.

10. A nucleotide sequence containing a compound of claim 8.

11. A deoxyribonucleic acid sequence containing a base of the formula:

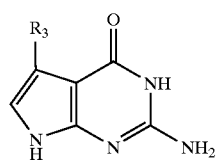

wherein $R_1$ is a $C_{1-10}$ alkyl group substituted by hydroxyl, $C_{1-4}$ alkoxy or halo.

12. Method for determining the nucleotide base sequence of a DNA molecule comprising the steps of:

incubating a DNA molecule annealed with a primer molecule able to hybridize to said DNA molecule in a vessel containing a molecule comprising the following moiety of formula (II):

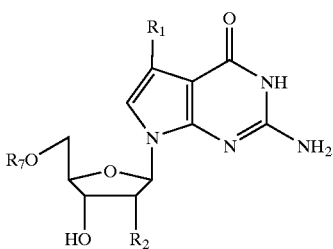

wherein $R_1$ is $C_{1-10}$ alkyl group substituted by hydroxyl, $C_{1-4}$ alkoxy or halo; $R_2$ is hydrogen and $R_7$ is a tri-phosphate or thiophosphate thereof; a DNA polymerase and at least one DNA synthesis terminating agent which terminates DNA synthesis at a specific nucleotide base in an incubating reaction; and separating DNA products of the incubating reaction according to size whereby at least a part of the nucleotide base sequence of said DNA molecule can be determined.

13. The method of claim 12, wherein said molecule containing a moiety of formula (II) is a compound of formula (II).

14. The method of claim 12, wherein said moiety of formula (II) is 7-Hydroxymethyl-7-deaza-2'-deoxyguanosine.

15. Method for elongation of an oligonucleotide sequence comprising the step of:

incubating an oligonucleotide sequence with a molecule comprising the following moiety of formula (II):

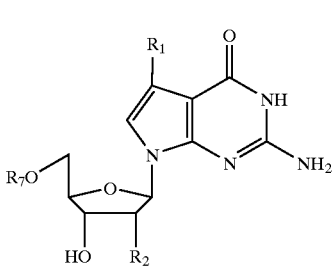

wherein $R_1$ is $C_{1-10}$ alkyl group substituted by hydroxyl, $C_{1-4}$ alkoxy or halo; $R_2$ is hydrogen; and $R_7$ is a tri-phosphate or thiophosphate thereof, and a DNA polymerase such that said molecule is added to the oligonucleotide sequence.

16. The method of claim 15, wherein said molecule containing a moiety of formula (II) is a compound of formula (II).

17. A compound of the formula (III):

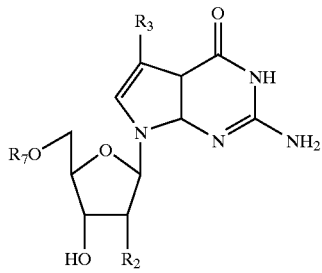
(III)

wherein $R_2$ is hydrogen or hydroxyl and $R_3$ is $C_{2-10}$ alkynyl group substituted by hydroxyl, $C_{1-4}$ alkyl substituted amino, $C_{1-4}$ alkoxy or halo, and $R_7$ is a mono-, di-, or tri-phosphate or thiophosphate thereof.

18. A process for the preparation of a compound of the formula (II) wherein $R_1$ is $C_{1-10}$ alkyl group substituted by hydroxy, $C_{1-4}$ alkoxy or halo; $R_2$ is hydrogen and $R_7$ is H or a mono-, di-, or tri-phosphate or thiophosphate thereof, which comprises:

(i) the deprotection of a compound of the formula (IV):

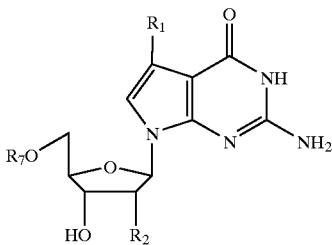
(IV)

wherein $R_1$ is $C_{1-10}$ alkyl group substituted by hydroxy, amino, $C_{1-4}$ alkoxy or halo and $R_4$ is a protecting group, $R_5$ is hydrogen and $R_6$ is a protecting group which is the same or different to $R_4$, or (ii) wherein $R_1$ is other than methyl the reduction of a compound of the formula (III)

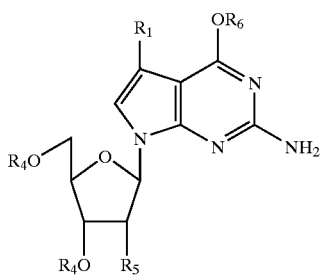
(III)

wherein $R_2$ is hydrogen, $R_3$ is $C_{2-20}$ alkynyl group substituted by hydroxyl, amino, $C_{1-14}$ alkyl substituted amino, $C_{1-4}$ alkoxy or halo, and $R_7$ is H or a mono-di-, or tri-phosphate thereof;

(iii) and optionally thereafter preparing a mono-, di-, or triphosphate or thiophosphate.

19. A compound of formula (II):

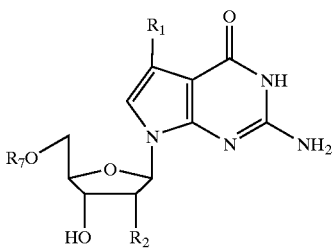
(II)

wherein $R_1$ is an isopropyl group; $R_2$ is hydrogen or hydroxyl; and $R_7$ is a mono-, di- or tri-phosphate or thiophosphate thereof.

20. A method for determining the nucleotide base sequence of a DNA molecule comprising the steps of:

incubating a DNA molecule annealed with a primer molecule able to hybridize to said DNA molecule in a vessel containing a compound of formula (II):

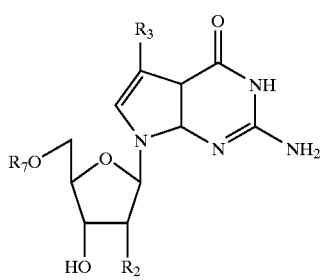
(II)

wherein $R_1$ is an isopropyl group; $R_2$ is hydrogen or hydroxyl; and $R_7$ is a tri-phosphate or thiophosphate thereof; a DNA polymerase, and at least one DNA synthesis terminating agent which terminates DNA synthesis at a specific nucleotide base in an incubating reaction; and separating DNA products of the incubating reaction according to size whereby at least a part of the nucleotide base sequence of said DNA molecule can be determined.

* * * * *

UNITED STATES PATENT AND TRADEMARK OFFICE
CERTIFICATE OF CORRECTION

PATENT NO. : 6,906,185 B1  Page 1 of 1
APPLICATION NO. : 09/045732
DATED : June 14, 2005
INVENTOR(S) : Fuller et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by (317) days Delete the phrase "by 317" and insert -- by 0 days--

Signed and Sealed this

Thirtieth Day of October, 2007

JON W. DUDAS
*Director of the United States Patent and Trademark Office*